(12) United States Patent
Qi et al.

(10) Patent No.: US 11,523,799 B2
(45) Date of Patent: Dec. 13, 2022

(54) FETAL IMAGING SYSTEM AND METHOD

(71) Applicant: KONINKLIJKE PHILIPS N.V., Eindhoven (NL)

(72) Inventors: Yu Qi, Shanghai (CN); Jian Gang Chen, Shanghai (CN); Lin Li, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 753 days.

(21) Appl. No.: 16/081,274

(22) PCT Filed: Mar. 6, 2017

(86) PCT No.: PCT/EP2017/055114
§ 371 (c)(1),
(2) Date: Aug. 30, 2018

(87) PCT Pub. No.: WO2017/153301
PCT Pub. Date: Sep. 14, 2017

(65) Prior Publication Data
US 2021/0219949 A1 Jul. 22, 2021

(30) Foreign Application Priority Data

Mar. 9, 2016 (WO) ................ PCT/CN2016/075977
May 10, 2016 (EP) .................................... 16168847

(51) Int. Cl.
*A61B 8/08* (2006.01)
*A61B 8/00* (2006.01)
(52) U.S. Cl.
CPC .......... *A61B 8/0866* (2013.01); *A61B 8/4254* (2013.01); *A61B 8/4472* (2013.01); *A61B 8/461* (2013.01); *A61B 8/5207* (2013.01)

(58) Field of Classification Search
CPC ....... A61B 8/0866; A61B 8/13; A61B 8/4254; A61B 8/4444; A61B 8/463; A61B 8/466;
(Continued)

(56) References Cited

U.S. PATENT DOCUMENTS 7,399,278 B1 7/2008 Ross
2008/0146932 A1* 6/2008 Chalana ............... A61B 8/0866
600/447
(Continued)

FOREIGN PATENT DOCUMENTS

EP 2636374 A1 9/2013
JP H05277109 A 10/1993
(Continued)

OTHER PUBLICATIONS

Moshiri et al.: Comprehensive Imaging Review of Abnormalities of the Umbilical Cord, Jan. 1, 2014, RadioGraphics 2014, vol. 34, No. 1, (p. 179-196) (Year: 2014).*
"Accelerometer." Wikipedia, Wikimedia Foundation, Oct. 10, 2021, https://en.wikipedia.org/wiki/Accelerometer. (Year: 2021).*
"Gyroscope." Wikipedia, Wikimedia Foundation, Oct. 20, 2021, https://en.wikipedia.org/wiki/Gyroscope (Year: 2021).*
(Continued)

*Primary Examiner* — Yi-Shan Yang

(57) ABSTRACT

An ultrasound fetal imaging system uses an acceleration sensor (16) for generating an acceleration signal relating to movement of the ultrasound transducer (10). A user is guided in how or where to move the ultrasound transducer based on the results of image processing of the ultrasound images. The user can thus be guided to move the transducer in a certain direction so as to achieve a complete scan of a fetus in a shortest possible time. This limits exposure of the expectant mother to the ultrasound energy. The fetal image obtained may be used to determine a fetal weight, for example using regression analysis based on some of the parameters derived from the obtained image.

21 Claims, 3 Drawing Sheets

(58) Field of Classification Search
CPC ......... A61B 8/483; A61B 8/523; A61B 8/461; G06T 2207/30044
See application file for complete search history.

(56) References Cited

U.S. PATENT DOCUMENTS

| | | | |
|---|---|---|---|
| 2008/0167553 A1* | 7/2008 | Paltieli | A61B 8/0866 600/437 |
| 2008/0167581 A1* | 7/2008 | Paltieli | A61B 5/435 600/588 |
| 2009/0093716 A1* | 4/2009 | Deischinger | A61B 8/13 600/443 |
| 2009/0093717 A1* | 4/2009 | Carneiro | G06F 19/00 600/443 |
| 2010/0125201 A1 | 5/2010 | Fujii | |
| 2011/0079083 A1 | 4/2011 | Yoo et al. | |
| 2013/0053697 A1* | 2/2013 | Holl | G01S 7/52096 600/459 |
| 2013/0237824 A1* | 9/2013 | Kim | A61B 8/466 600/440 |
| 2014/0031688 A1 | 1/2014 | Perrey et al. | |
| 2014/0200449 A1 | 7/2014 | Yoo | |
| 2015/0173715 A1 | 6/2015 | Raghavan | |
| 2015/0374344 A1 | 12/2015 | Koide | |
| 2016/0259898 A1* | 9/2016 | Kim | A61B 8/4444 |
| 2017/0245835 A1* | 8/2017 | Okazaki | G06T 7/73 |

FOREIGN PATENT DOCUMENTS

| | | |
|---|---|---|
| JP | 2010259662 A | 11/2010 |
| JP | 2013017870 A | 1/2013 |
| WO | WO2004041094 A2 | 5/2004 |
| WO | WO2014141277 A1 | 9/2014 |
| WO | WO2015036991 A1 | 3/2015 |
| WO | WO2017003905 A1 | 1/2017 |

OTHER PUBLICATIONS

Melamed, N. et al., "Sonographic Fetal Weight Estimation: Which Model Should be Used?" American Institute of Ultrasound in Medicine, J. Ultrasound Med. 2009; 28(5): 617-29.

Shittu, A.S. et al., "Clinical Versus Sonographic Estimation of Fetal Weight in Southwest Nigeria", J Health Popul Nutr. 2007; 25(1): 14-23.

Holmes, F. T. et al., "The Effect of Body Mass Index on Three Methods of Fetal Weight Estimation", BJOG: an International Journal of Obstetrics and Gynecology, Jun. 2002; vol. 109, pp. 651-657.

Gibbs, V. et al., "Ultrasound Physics and Technology How, Why and When", London, UK: Churchill Livingstone, Radiography (2010) 16, 167.

"Radiation Emitting Products", Medical Imaging > Ultrasound Imaging, Downloaded from the Internet Aug. 28, 2018, http://www.fda.gov/Radiation-EmittingProducts/RadiationEmittingProductsandProcedures/MedicalImaging/ucm115357.htm#benefitsrisks.

"Ultrasound Detection of Nuchal Cord Prior to Labor Induction and the Risk of Cesarean Section", Ultrasound Obstet Gynecol. Feb. 2005;25(2):160-164.

Singh, Lt Col G. et al., "Nuchal Cord: A Retrospective Analysis", MJAFI, vol. 64, No. 3 Med J Armed Forces India. Jul. 2008;64(3):237-40.

Reed, R. B. et al., "Nuchal Cords: Sharing the Evidence with Parents", British Journal of Midwifery, Feb. 2009, vol. 17 (2): 106-109.

Reed, R. et al., "Nuchal Cords: Think Before You Check", The Practising Midwife, vol. 10, No. 5, pp. 18-20, May 2007.

PCT International Search Report, International application No. PCT/EP2016/055114, dated Apr. 20, 2017.

\* cited by examiner

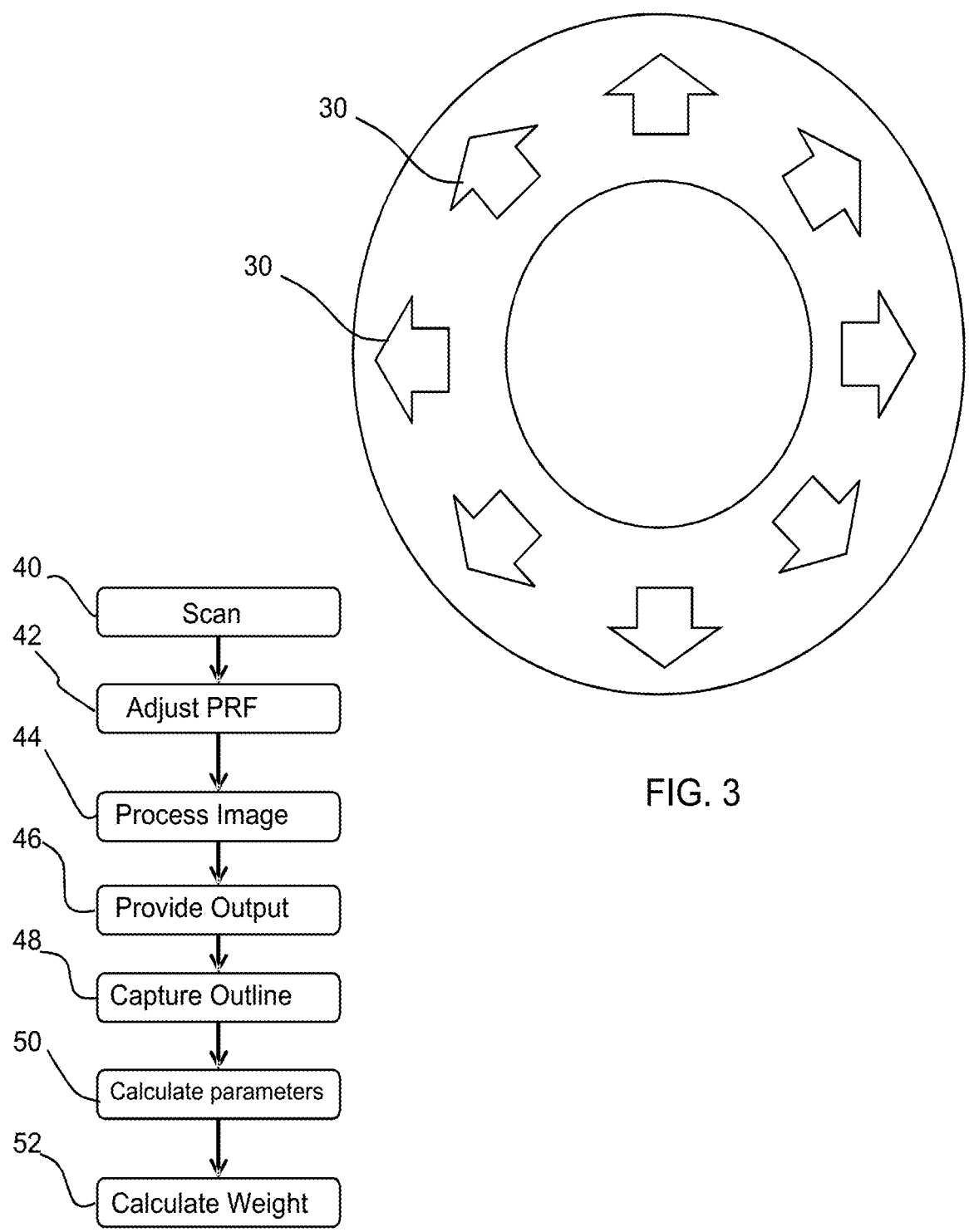

FETAL IMAGING SYSTEM AND METHOD

CROSS-REFERENCE TO RELATED APPLICATIONS

This application claims the priority benefit under 35 U.S.C. § 371 of International Patent Application No. PCT/EP2017/055114, filed Mar. 6, 2017, which claims the benefit European Patent Application No. EP16168847.8, filed May 10, 2016 and PCT/CN2016/075977 filed Mar. 9, 2016. These applications are hereby incorporated by reference herein in their entirety.

FIELD OF THE INVENTION

This invention relates to a fetal imaging system and method.

BACKGROUND OF THE INVENTION

One purpose of fetal imaging is to provide an estimation of the fetal weight.

Accurate estimation of fetal weight has an important role in routine antenatal care and for detection of fetal growth abnormalities.

The two main methods for predicting birth-weight in current obstetric practice are firstly clinical estimation based on abdominal palpation of fetal soma parts and measurement of the fundal height, and secondly sonographic measurements of skeletal fetal parts which are then inserted into regression equations to derive estimated fetal weight. Compared to other methods, ultrasound estimation is the most accurate method for fetal weight estimation.

Studies have been done to compare the accuracy of the methods for estimation of birth weight just before birth, and found the accuracy of ultrasound estimation was better than clinical estimation of fetal weight.

Ultrasound estimated fetal weight is obtained from two dimensional ultrasound measurements of fetal parts. As mentioned above, these measurements are used in a regression formula to derive a fetal weight. The regression models are based on combinations of different fetal biometric indices, mainly the abdominal circumference (AC), the femur length (FL), the biparietal diameter (BPD), and the head circumference (HC).

Table 1 shows a table of regression indices used to estimate fetal weight from different combinations of these parameters.

| Fetal biometric indices | Regression equation |
|---|---|
| AC | Ln EFW = −4.564 + 0.282(AC) − 0.00331(AC)$^2$ (†) |
|  | Ln EFW = 2.695 + 0.253(AC) − 0.00275(AC)$^2$ |
|  | Log$_{10}$ EFW = 0.6328 + 0.1881(AC) − 0.0043(AC)$^2$ + 0.000036239(AC)$^3$ |
|  | Log$_{10}$ = −1.8367 + 0.092(AC) − 0.000019(AC)$^3$ (†) |
|  | EFW = 0.0816(AC)$^3$ |
| AC and FL | Log$_{10}$ EFW = 1.304 + 0.05281(AC) + 0.1938(FL) − 0.004(AC)(FL) |
|  | Log$_{10}$ EFW = 0.59 + 0.08(AC) + 0.28(FL) − 0.00716(AC)(FL) |
|  | Ln EFW = 2.792 + 0.108(FL) + 0.0036 (AC)$^2$ − 0.0027(FL)(AC) |
| AC and BPD | Log$_{10}$ EFW = 1.879 + 0.084(BPD) + 0.026(AC) (‡) |
|  | Log$_{10}$ EFW = −1.599 + 0.144(BPD) + 0.032(AC) − 0.000111(BPD)2(AC) (†) |
|  | Log$_{10}$ EFW = −1.7492 + 0.166(BPD) + 0.046(AC) − 0.002546(AC)(BPD) (†) |
|  | Log$_{10}$ EFW = −1.1683 + 0.0377(AC) + 0.0950(BPD) − 0.0015(BPD)(AC) (†) |
|  | Log$_{10}$ EFW = 1.1134 + 0.05845(AC) − 0.000604(AC)$^2$ − 0.007365(BPD)$^2$ + 0.000595(BPD)(AC) + 0.1694(BPD) |
|  | Log$_{10}$ EFW = 1.63 + 0.16(BPD) + 0.00111(AC)$^2$ − 0.0000859(BPD)(AC)$^2$ |
|  | Log$_{10}$ EFW = 2.1315 + 0.0056541(AC)(BPD) − 0.00015515(BPD)(AC)$^2$ + 0.000019782(AC)$^3$ + 0.052594(BPD) |
| AC and HC (±BPD) | Log$_{10}$ EFW = 1.182 + 0.0273(HC) + 0.07057(AC) − 0.00063 (AC)$^2$ − 0.0002184 (HC)(AC) |
|  | Log$_{10}$ EFW = 0.9119 + 0.0488(HC) + 0.0824(AC) − 0.001599(HC)(AC) |
|  | Log$_{10}$ EFW = 2.3231 + 0.02904(AC) + 0.0079(HC) − 0.0058(BPD) |
| AC, FL and BPD | Log$_{10}$ EFW = 1.335 − 0.0034(AC)(FL) + 0.0316(BPD) + 0.0457(AC) + 0.1623(FL) |
|  | Log$_{10}$ EFW = 1.54 + 0.15(BPD) + 0.00111(AC)$^2$ − 0.0000764 (BPD)(AC)$^2$ + 0.05(FL) − 0.000992(FL)(AC) |
|  | EFW = 0.23966(AC)$^2$(FL) + 1.6230(BPD)$^3$ |
|  | Log$_{10}$ EFW = 2.7193 + 0.0094962(AC)(BPD) − 0.1432(FL) − 0.00076742(AC)(BPD)$^2$ + 0.001745(FL)(BPD)$^2$ |
| AC, FL and HC | Log$_{10}$ EFW = 1.326 − 0.00326(AC)(FL) + 0.0107(HC) + 0.0438(AC) + 0.158(FL) |
|  | EFW = 0.23718(AC)$^2$(FL) + 0.03312(HC)$^3$ |
|  | Log$_{10}$ EFW = −2.0661 + 0.04355(HC) + 0.05394(AC) − 0.0008582(HC)(AC) + 1.2594(FL/AC) (†) |
| AC, FL, BPD and HC | Log$_{10}$ EFW = 1.3596 + 0.0064(HC) + 0.0424(AC) + 0.174(FL) + 0.00061(BPD)(AC) − 0.00386(AC)(FL) |

In this table, EFW is the estimated fetal weight; AC is the abdominal circumference; FL is the femur length; BPD is the biparietal diameter; HC is the head circumference. AC, FL, BPD, and HC are generally expressed in centimeters, and EFW is generally expressed in grams. The exceptions to this are shown as †: Estimated fetal weight is expressed in kilograms and ‡: Femur length is expressed in millimeters.

This table is taken from Melamed N, Yogev Y, Meizner I, Mashiach R, Bardin R and Ben-Haroush A. "Sonographic fetal weight estimation: which model should be used?" J, Ultrasound Med. 2009; 28(5): 617-29.

In addition to monitoring in a clinical environment, measurement of fetal weight at home may be used to help a pregnant woman to understand their babies' growth trend and wellbeing, and the pregnant woman can also estimate how much weight she has gained herself. However, there is no home-use fetal weight measurement device available currently.

As explained above, ultrasound is the most accurate method for fetal weight estimation, but it only be used in clinics by experienced doctors. In addition, the energy of ultrasound used in clinics is a concern. Both clinical and home-use ultrasound device should follow the general principle of ultrasound exposure named ALARA (as low as reasonably achievable), and according to regulations, the power output of ultrasound systems for the fetus should be limited to 720 mW/cm$^2$. Even though no study has reported adverse effects relating to performing sonograms on the fetus in clinics, the safety of ultrasound device for home use is a concern. Thus lowering the ultrasound exposure as much as possible will be always welcomed by consumers.

Another issue which requires monitoring during pregnancy is the occurrence of a nuchal cord. This arises when the umbilical cord becomes wrapped around the fetal neck by a full 360 degrees. Nuchal cords are very common, with reported prevalence rates of 10% to 37%.

The nuchal cord occurs more commonly in male babies. It can arise during pregnancy or in labor but is progressively more likely towards the end of the gestation period.

Maternity care providers are expected to encounter nuchal cords regularly in their practice.

The fetal umbilical cord is an important bridge to transmit nutrition, because it is the essential channel for exchanging blood and gas between the maternal womb and fetus. A nuchal cord may affect fetal blood and gas exchange, alter the fetal blood supply, and in severe cases cause fetal hypoxia leading to stillbirths and neonatal deaths. In addition, it significantly affects the descent of the fetal head and fetal blood circulation, which may cause fetal intrauterine hypoxia, asphyxia and even death.

The nuchal cord is generally checked by monitoring the fetal movement by the mother subjectively at home, which is inconvenient and sometimes with high risk. For example, the mother may miss important signs of a nuchal cord if she does not pay attention to the baby's movement.

In addition, many birth practitioners are trained to routinely check for a nuchal cord during the second stage of labor, and if present, intervene further by pulling to unloop the cord, or clamping and cutting. Currently, the diagnosis of a nuchal cord is most often performed using ultrasound in hospitals.

As explained above, ultrasound systems require trained operatives and are generally used only in a clinical environment.

EP2636374A1 discloses a method of marking a cut line or a cut surface on a 3-dimensional (3D) ultrasound image of an object which is obtained by using a probe, wherein the cut line and the cut surface are used to view a cross section of the 3D ultrasound image, detecting motion information about the probe by using a sensor included in the probe, and changing a location of the cut line or the cut surface based on the detected motion information about the probe.

US20150374344A1 discloses an apparatus comprising an ultrasonic probe for performing transmission/reception of ultrasound on a subject, a movement detecting section for detecting movement of an ultrasonic scan plane by said ultrasonic probe, a storage section for storing therein information on positions of a plurality of first scan planes in a first three-dimensional (3D) ultrasonic scan on said subject; and an image display control section for displaying in a display section a first image representing positions of said first scan planes based on said information on positions stored in said storage section, and displaying in said display section, based on detected information from said movement detecting section, a second image representing positions of a plurality of second scan planes formed by performing a second 3D ultrasonic scan on said subject by an operator moving said ultrasonic probe, said image display control section displaying said first and second images so that said first scan planes and second scan planes have mutually corresponding positional relationships.

WO2014141277A1 discloses a probe for use in monitoring one or more parameters of a subject, the probe comprising a monitoring assembly comprising at least one acoustic port for transmitting acoustic radiation into a region of interest in the subject, at least one light output port for transmitting incident light towards the region of interest, and at least one light input port for receiving light returned from the subject, and at least one control mechanism comprising at least one sensing assembly configured for sensing at least one of proximity attachment and signal quality conditions, and being configured for controlling a condition of coupling between the probe assembly and the subject, enabling to control operation of the monitoring assembly.

US20100125201A1 discloses an ultrasound imaging apparatus having a probe configured to transmit ultrasound and receive reflected waves, a generator configured to generate an image based on said reflected waves, and a display that displays said image, wherein the ultrasound imaging apparatus comprising, a first analyzer configured to specify respectively each umbilical cord present in said image, a second analyzer configured to respectively specify a structure continuing into one end of said umbilical cord and a display controller configure to cause each said structure to be displayed on said identified and display.

SUMMARY OF THE INVENTION

It would be desirable to have a fetal imaging system based on ultrasound which is easier to use and enables accurate determination of fetal weight and/or the presence of a nuchal cord.

The invention is defined by the claims.

According to examples in accordance with an aspect of the invention, there is provided a fetal imaging system, comprising:

an ultrasound transducer;

an acceleration sensor for generating an acceleration signal relating to movement of the ultrasound transducer;

an output for providing output information to guide a user of the system in respect of moving the ultrasound transducer;

an image processing module for processing the ultrasound images generated by the ultrasound transducer; and a controller for controlling the ultrasound transducer and the output information in dependence on the acceleration signal and the results of the ultrasound image processing; wherein the results of the ultrasound image processing are the fetal body portion recognized by the image processing module.

In this system, the movement of an ultrasound transducer is tracked by an acceleration sensor, so that a user can be guided to move the transducer in a certain direction so as to achieve a complete scan of a fetus in a shortest possible time when the transducer is activated. The obtained results of the ultrasound image processing are the fetal body portions recognized by the image processing, for example flesh or bones of the fetus, which provide indications for a shortest route during the scanning. This limits exposure of the expectant mother to the ultrasound energy. The fetal image obtained may be used to determine a fetal weight, for example using regression analysis based on some of the parameters derived from the obtained image.

The controller may be adapted to control the emission of ultrasound signals in dependence on the movement of the ultrasound transducer or on the ultrasound image quality.

Ultrasound signals may thus be generated only when needed to further build the desired ultrasound image. For example, if the ultrasound transducer is stationary, the transducer may stop being activated if the ultrasound image is successfully captured, until a new transducer position has been selected by the user. The controller may alternatively control the ultrasound transducer based on image quality. The ultrasound transducer, for example the emission power or the operation modes, may be controlled accordingly to achieve a tolerant resolution for fetal detection so that the exposure to the ultrasound signals is limited as much as possible.

The controller may be adapted to control the emission power of the ultrasound transducer in dependence on a speed of movement of the ultrasound transducer.

In this way, even while the transducer is moving, the emission power of the ultrasound transducer may be adjusted so as to achieve a desired resolution of the overall image while keeping exposure levels as low as possible. The control of the emission power may be implemented by automatic or semi-automatic shifts between the operation modes of the ultrasound transducer.

The image processing module may be adapted to detect fetus edges from the results of the ultrasound image processing and the controller is adapted to control the ultrasound transducer and the output information in dependence on the acceleration signal and the fetus edges detected.

The controller may be adapted to control the output to provide an indication of a direction to move the ultrasound transducer to move towards a fetus or around the edge of the fetus. In this way, the user can be guided towards the fetus until the edge is found, and can then be guided around the edge. In this way, the outer contour of the fetus is imaged with limited ultrasound emission, and this enables the key indices to be measured or derived by image analysis, which includes FL, BPD, HC, fetal weight or other possible parameters. The imaging of the whole belly is avoided while only the partial area covering the fetal edges is exposed to the ultrasound signals, which limits the possibility of over exposure. The detections are based on results of the ultrasound image processing, where the fetal portion, for example the flesh or the bones of the fetus, is recognized from the other environmental tissues, for example amniotic fluid. The fetal body portion recognized may optionally be the heart, neck, leg or other body portion. Then the controller will instruct the user to move accordingly to the fetal edges based on anatomical knowledges.

The controller may also be adapted to control the output to provide an indication of a speed with which to move the ultrasound transducer.

The output for example comprises a display device or a wireless signal to be provided to a remote display device. The system may for example communicate with a remote display or it may have a display as an integrated part of the system. It may also use sound output. This enables the ultrasound image to be viewed as well as instructions for the user. Alternatively or additionally, indicator lights may be used to provide directional instructions to the user.

The ultrasound transducer may be fixed to a pad having a surface for pressing against the abdomen, wherein the ultrasound transducer output is directed perpendicularly to the pad surface.

This arrangement ensures that the output is directed normally into the abdomen and the system is easy to use. In addition, it prevents an ultrasound signal being received by the user out from of the imaging focusing area.

The controller may be adapted to generate an output to direct the user to move the ultrasound transducer to take an image of the neck region of the fetus, and the image processing module is adapted to recognize a neck region and detect a blood flow direction thereby to identify a suspected nuchal cord based on the blood flow direction relative to the neck region.

Doppler image processing may be used to identify the blood flow direction. A blood flow direction perpendicular to neck region, which is the line between the heart and head, is indicative of a nuchal cord, whereas a direction parallel to the line between the heart and head is indicative of the carotid artery.

The image processing module may for example be adapted to identify the neck region by identifying the heart and head.

Examples in accordance with another aspect of the invention provide a fetal imaging method, comprising:

taking an ultrasound image using an ultrasound transducer based on a sequence of images at different ultrasound transducer positions;

generating an acceleration signal relating to movement of the ultrasound transducer;

outputting information to guide a user of the method to move the ultrasound transducer during the sequence;

processing the ultrasound images generated by the ultrasound transducer during the sequence; and controlling the ultrasound transducer and the output information in dependence on the acceleration signal and the results of the ultrasound image processing.

In this method, the user is guided to move the transducer in a certain direction so as to achieve a complete scan of a fetus in a shortest possible time. This limits exposure of the expectant mother to the ultrasound energy.

The method may comprise controlling the ultrasound transducer in dependence on the movement (i.e. position and/or speed) of the ultrasound transducer. This limits the exposure of the expectant mother.

The method may comprise detecting fetus edges, and controlling the output to provide an indication of a direction to move the ultrasound transducer to move towards a fetus or around the edge of the fetus.

An output may be generated to direct the user of the method to move the ultrasound transducer to take an image of the neck region of the fetus, and the method then comprises detecting a blood flow direction thereby to identify a suspected nuchal cord.

The methods may be implemented at least in part in software.

BRIEF DESCRIPTION OF THE DRAWINGS

Examples of the invention will now be described in detail with reference to the accompanying drawings, in which:

FIG. 3 shows one example of a set of indicator lights to be used by the system of FIG. 2;

FIG. 4 shows the steps of an imaging and image processing method;

DETAILED DESCRIPTION OF THE EMBODIMENTS

The invention provides provided an ultrasound fetal imaging system which uses an acceleration sensor for generating an acceleration signal relating to movement of the ultrasound transducer. A user is guided in how or where to move the ultrasound transducer based on the results of image processing of the ultrasound images. The user can thus be guided to move the transducer in a certain direction so as to achieve a complete scan of a fetus in a shortest possible time. This limits exposure of the expectant mother to the ultrasound energy. The fetal image obtained may be used to determine a fetal weight, for example using regression analysis based on some of the parameters derived from the obtained image.

Figure 1:
FIG. 1 shows a standard ultrasound image.

FIG. 1 shows an ultrasound image of a fetus. As can be seen, it has bright edge regions at the boundaries between regions of different tissue density, which results in high contrast difference in the ultrasound image obtained. Thus, the outline of the skeletal parts as well as the flesh in the field of view can easily be identified by image processing due to the contrast difference. It enables the determination of outlier of the fetus with low resolution imaging.

Figure 2:
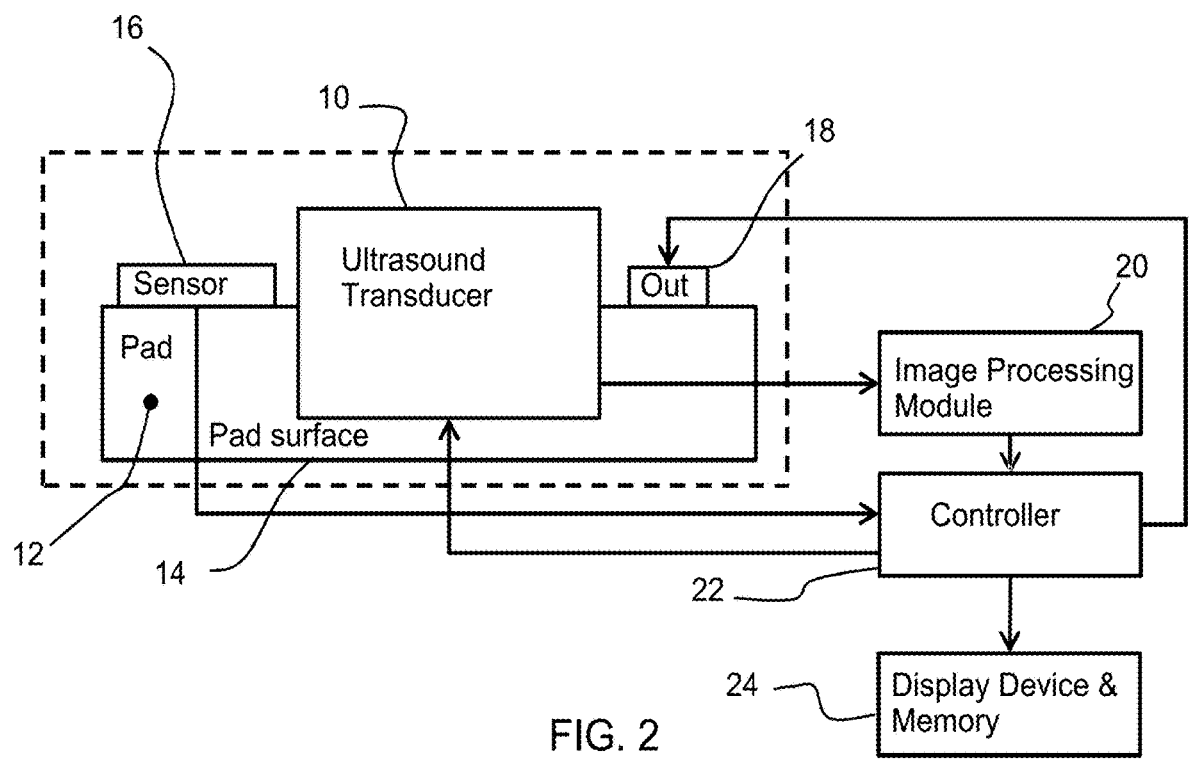
FIG. 2 shows an ultrasound system.

FIG. 2 shows the fetal imaging system. It comprises an ultrasound transducer 10 mounted on a pad 12 for application to the skin. The ultrasound transducer can have a single element or an array of elements. The ultrasound transducer directs an ultrasound beam in a direction normal to the surface 14 of the pad, so that the radiation is directed normally into the skin. The ultrasound transducer receives an echo signal for subsequent image processing and analysis. The pad 12 surrounds the ultrasound transducer to keep the ultrasound transducer perpendicular to the measurement site in order to acquire consistent signals. The pad is made of a material with a higher rigidity than the skin and a material which does not irritate the skin. The ultrasound transducer can be linear or curved in 2D or 3D.

The ultrasound probe does not capture the full image shown in FIG. 1 from a single location. Instead, the overall image is made up by tiling multiple images from different ultrasound transducer positions.

The number of imaging positions used to build up the whole image depends for example on the fetal size. Taking a 2D image as an example, the typical frame rate is in the range 30-100 Hz. If operating at the lowest frame rate of 30 Hz, and with a moving speed of the transducer of 2 cm per second, this corresponds to 15 images per cm of movement. The frame rate may be lower for lower resolution imaging.

An acceleration sensor 16 is provided for generating an acceleration signal relating to movement of the ultrasound transducer 10.

An output device 18 is used to provide output information to guide a user of the system in respect of moving the ultrasound transducer 10. The output device may be an integral part of the system as shown, or it may be a remote device such as a smart phone with which the remainder of the system communicates. The output device may use light or sound or a combination. The aim is to guide an inexperienced user to move the transducer in the right direction to find the edge of fetal body and then move along the edge.

An image processing module 20 is used to process the ultrasound images generated by the ultrasound transducer 10.

A controller 22 is used to control the ultrasound transducer and also control the output provided to the user, in dependence on the acceleration signal and the results of the ultrasound image processing. Thus, the inputs to the controller come from the image processing module and the acceleration sensor. Other inputs may be provided, for example other position tracking information relating to the position of the ultrasound transducer. The controller provides outputs to the ultrasound transducer 10 and to the output device 18.

A separate display device and memory are shown as 24. This enables the analysis results to be stored for display and further analysis.

To overcome the problems of using ultrasound at home for fetal weight measurement, this system is able to use reduced energy levels, and it may be easy for untrained users to use the system by providing automatic guidance for the user.

In particular, the system enables reduced ultrasound exposure time to be achieved, and consequently reduced energy exposure, in order to measure the fetal weight at home by untrained people. The acceleration sensor 16 monitors whether the ultrasound transducer is moving and how fast it is moving. If the ultrasound transducer 10 stops moving, the system is able to detect this and thereby stop generating ultrasound signals.

In addition, the pulse repeating frequency (PRF) of the ultrasound imaging process can be adjusted according to the speed of movement of the transducer. When the ultrasound transducer moves slowly, the PRF may thus be reduced in order to avoid over-exposure to the ultrasound energy. By providing automatic adjustment of the PRF in this way, this device may for example send at most two imaging pulses at each location passed by the ultrasound transducer.

Clinical devices may for example send 20 to 30 ultrasound pluses per second. A lower pulse repetition rate may be sufficient for home use to obtain an outline of the fetus which can then be used for fetal weight estimation. One pulse in this context means one transmit signal from each transducer element in the array simultaneously, enabling analysis of the combined echo signal to form a part of the ultrasound image which corresponds to the particular location of the ultrasound transducer.

FIG. 3 shows an example of the output device 18 which may be used to guide the user. It comprises a set of indicator lights 30 which indicate to a user the direction in which the transducer element should be moved. The indicator lights may be used to guide the user where to move the transducer element in order to find the edge of the fetal body, and then to move along the edge based on the image analysis.

Once the whole outline of the fetal body has been obtained, the indicator lights can then give a completion indication (for example all flashing). Sound guidance may also be given, not only to assist in following the correct movement direction, but also to alert if any errors occurs, for example if the user is moving too fast or in the wrong direction.

After scanning is complete, an image of the outline of the fetal body can be generated, the key fetal biometric parameters can then be measured or derived automatically, and the fetal weight can be calculated by using a suitable regression formula. The biometric parameters may be obtained by the image processing module 20.

By monitoring results over time, a fetal growth curve may for example be obtained, for example for viewing from a smart phone.

FIG. 4 shows the method steps employed by the system. Note that these steps do not follow strictly in order, since some steps are performed at the same time as others. For example, the image analysis takes place in real time all the time the imaging is being carried out.

In step 40, the transducer is used to scan the abdomen of pregnant women. The transducer starts to emit ultrasound signal once it moves, which is determined by the accelerometer embodied with the transducer. Thus, during the scanning of step 40, an acceleration sensor signal is generated to determine the movement direction and speed of the transducer. At each location the transducer passes, the system may set a maximum number of imaging pulses, for example at most two imaging pluses.

In step 42, the PRF is automatically adjusted according to the moving speed of the transducer in order to avoid over exposure to the ultrasound energy when the transducer moves too slowly or is kept still. To facilitate the usage by inexperienced people, the transducer is designed to be always perpendicular to the measurement site while moving by means of the pad surrounding the ultrasound transducer.

In step 44, the image processing module processes and analyzes captured images. The edge of the fetus is determined by the strong contrast between the fetal body and amniotic fluid.

In step 46, an output in the form of an indicator light and/or sound is used to inform the user in which direction the transducer should be moved towards in order to find the edge of the fetal body and then to move along the edge. This direction information is obtained from the real time image analysis in step 44. Thus, in this way, the user is guided to image the whole outline of the fetus. This edge detection can be based on finding the strongest contrast, which is the boundary between the amniotic fluid and the fetal body, and directing the transducer to move along the length direction of this line between the bright image part, i.e. the fetal body, and the dark image part, i.e. the amniotic fluid. An alert can be given if moving speed is too high or the moving direction is wrong.

In step 48, once the outline of fetal body is captured, the device informs the user to stop scanning.

Based on the captured fetal body outline picture, the key fetal body biometric parameters can be calculated automatically in step 50. By using a suitable regression formula, the fetal weight can be calculated in step 52. A plot of the fetal weight over a longer period of time may also be generated.

Another use for the system is to detect nuchal cords for home use. The output device (indicator lights, sounds, or display data) may then include an output mode for indicating a nuchal cord.

A first step is to identify the heart by analyzing either the Doppler signal or B-mode images based on the specific motion pattern of the heart. The position of the transducer where the heart is identified is then recorded by the system, e.g., using an electromagnetic tracking system or a coordinate system such as used in a computer mouse. As an additional option, the heart beating pattern is stored each time when the user performs the scanning as historical data and this data may be analyzed if any abnormity is present.

Figure 5:
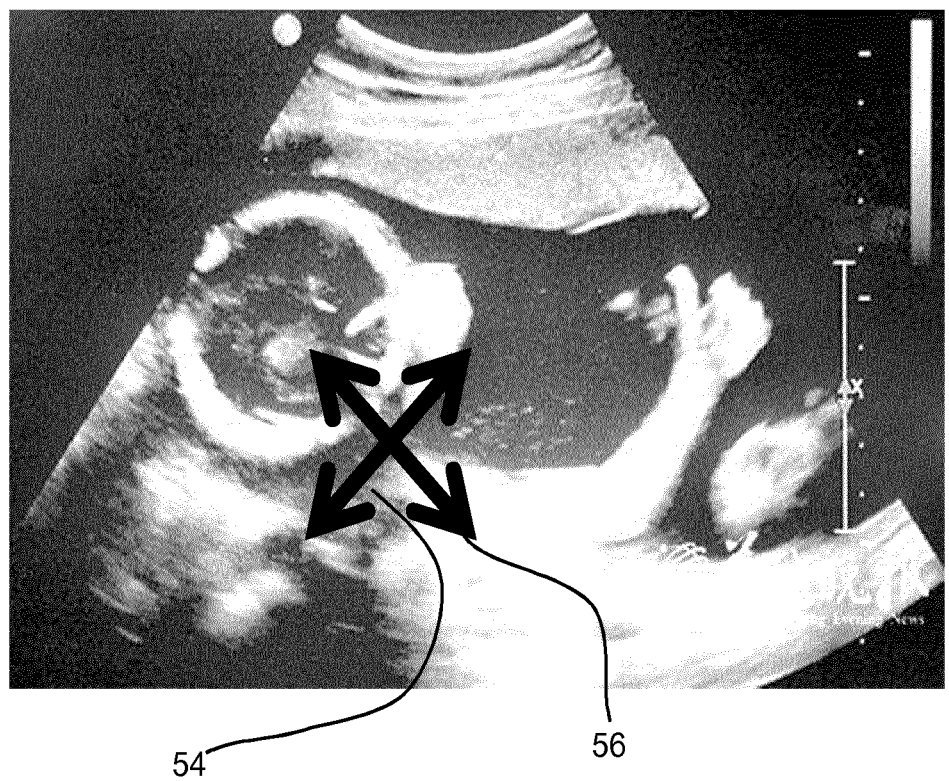
FIG. 5 shows an ultrasound image and explains how a nuchal cord can be detected.

A second step is to identify the skull. The skull is always clear on an ultrasound image, for example as seen in FIG. 5. Known image processing pattern recognition techniques may be used. The transducer position where the skull is recognized is also stored.

A third step is to check if there is any Doppler/color signal in the neck area. The neck can be identified because it is between the skull and heart as previously identified. The indicator lights may be used to direct the user to move the probe to the neck area by indicating moving directions in the same way as described above.

The blood flow direction in a nuchal cord is perpendicular to the line between the skull and heart, as shown by arrow 54 in FIG. 5. If such a direction is recognized, a nuchal cord is highly suspected. If the identified blood flow direction is found to be in parallel with the line between the skull and heart as shown by arrow 56 in FIG. 5, it may indicate the carotid.

The final step is to give the indication of potential nuchal cord. If nuchal cord is suspected, a warning signal is given, such as red lights.

The nuchal cord warning may be given without the need for the user to look at an ultrasound image at all. Indeed, no ultrasound image output is needed at all. Thus, no experience or training is needed to understand the warning given.

The system described above makes use of a controller or processor for processing the image data.

Figure 6:
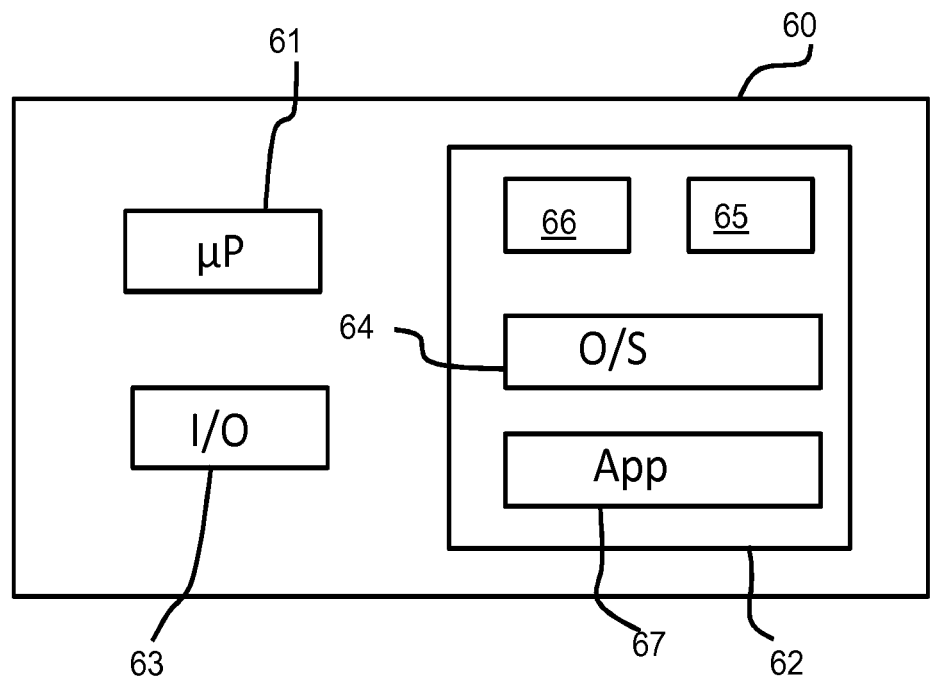
FIG. 6 shows a generic computer architecture suitable for use in performing the signal processing of the system of FIG. 2.

FIG. 6 illustrates an example of a computer 60 for implementing the controller or processor described above.

The computer 60 includes, but is not limited to, PCs, workstations, laptops, PDAs, palm devices, servers, storages, and the like. Generally, in terms of hardware architecture, the computer 60 may include one or more processors 61, memory 62, and one or more I/O devices 63 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 61 is a hardware device for executing software that can be stored in the memory 62. The processor 61 can be virtually any custom made or commercially available processor, a central processing unit (CPU), a digital signal processor (DSP), or an auxiliary processor among several processors associated with the computer 60, and the processor 61 may be a semiconductor based microprocessor (in the form of a microchip) or a microprocessor.

The memory 62 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 62 may incorporate electronic, magnetic, optical, and/or other types of storage media. Note that the memory 62 can have a distributed architecture, where various components are situated remote from one another, but can be accessed by the processor 61.

The software in the memory 62 may include one or more separate programs, each of which comprises an ordered listing of executable instructions for implementing logical functions. The software in the memory 62 includes a suitable operating system (O/S) 64, compiler 65, source code 66, and one or more applications 67 in accordance with exemplary embodiments.

The application 67 comprises numerous functional components such as computational units, logic, functional units, processes, operations, virtual entities, and/or modules.

The operating system 64 controls the execution of computer programs, and provides scheduling, input-output control, file and data management, memory management, and communication control and related services.

Application 67 may be a source program, executable program (object code), script, or any other entity comprising a set of instructions to be performed. When a source program, then the program is usually translated via a compiler (such as the compiler 65), assembler, interpreter, or the like, which may or may not be included within the memory 62, so as to operate properly in connection with the operating system 64. Furthermore, the application 67 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 63 may include input devices such as, for example but not limited to, a mouse, keyboard, scanner, microphone, camera, etc. Furthermore, the I/O devices 63 may also include output devices, for example but not limited to a printer, display, etc. Finally, the I/O devices 63 may further include devices that communicate both inputs and outputs, for instance but not limited to, a network interface controller (NIC) or modulator/demodulator (for accessing remote devices, other files, devices, systems, or a network), a radio frequency (RF) or other transceiver, a telephonic interface, a bridge, a router, etc. The I/O devices 63 also include components for communicating over various networks, such as the Internet or intranet.

When the computer 60 is in operation, the processor 61 is configured to execute software stored within the memory 62, to communicate data to and from the memory 62, and to generally control operations of the computer 60 pursuant to the software. The application 67 and the operating system 64 are read, in whole or in part, by the processor 61, perhaps buffered within the processor 61, and then executed.

When the application 67 is implemented in software it should be noted that the application 67 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A fetal imaging system, comprising:
   an ultrasound transducer;
   an acceleration sensor for generating an acceleration signal relating to at least one of a movement direction and a speed of the ultrasound transducer;
   an output for providing output information to guide a user of the fetal imaging system to move the ultrasound transducer in a direction to locate a fetal edge of a fetal body;
   an image processor adapted to execute instructions stored in a tangible, non-transitory computer readable medium to process ultrasound images generated by the ultrasound transducer; and
   a controller for controlling an emission power of the ultrasound transducer and adjusting the output information in dependence on the acceleration signal and results of the ultrasound image processing;
   wherein the results of the ultrasound image processing are a fetal body portion recognized by the image processor.

2. The fetal imaging system as claimed in claim 1, wherein the controller is adapted to control emission of an ultrasound signal from the ultrasound transducer in dependence on a movement of the ultrasound transducer or on ultrasound image quality.

3. The fetal imaging system as claimed in claim 1, wherein the controller is adapted to control the emission power of the ultrasound transducer in dependence on the speed of movement of the ultrasound transducer as detected by the acceleration sensor.

4. The system as claimed in claim 1, wherein the instructions when executed by the image processor further cause the image processor to detect the fetal edge from the results of the ultrasound image processing and the controller is adapted to control the emission power of the ultrasound transducer and adjust the output information in dependence on the acceleration signal and the fetal edge detected.

5. The fetal imaging system as claimed in claim 1, wherein the controller is adapted to control the output to provide an indication of a direction to move the ultrasound transducer, the indication including the direction to be at least one of towards the fetal body or around the fetal edge.

6. The fetal imaging system as claimed in claim 5, wherein the controller is adapted to control the output to provide an indication of a speed with which to move the ultrasound transducer.

7. The fetal imaging system as claimed in claim 1, wherein the output comprises a display device or a wireless signal to be provided to a remote display device.

8. The fetal imaging system as claimed in claim 1, wherein the ultrasound transducer is fixed to a pad having a surface for pressing against an abdomen, wherein an ultrasound signal from the ultrasound transducer is directed perpendicularly to the pad surface.

9. The fetal imaging system as claimed in claim 1, wherein the controller is adapted to generate the output information to direct the user to move the ultrasound transducer to take an image of a neck region of the fetal body, and the instructions when executed by the image processor further cause the image processor to recognize the neck region and detect a blood flow direction thereby to identify a suspected nuchal cord based on the blood flow direction relative to the neck region.

10. The fetal imaging system as claimed in claim 9, wherein the instructions when executed by the image processor further cause the image processor to identify the neck region by identifying a heart and a head.

11. The fetal imaging system as claimed in claim 1, wherein at each location the ultrasound transducer passes, the fetal imaging system sets a maximum number of imaging pulses based on the acceleration signal.

12. A fetal imaging method, comprising:
   taking an ultrasound image using an ultrasound transducer;
   generating an acceleration signal relating to at least one of a movement direction and a speed of the ultrasound transducer used in taking the ultrasound image;
   outputting information to guide a user of the fetal imaging method to move the ultrasound transducer, in response to the acceleration signal, in a direction to locate a fetal edge of a fetal body;
   controlling an emission power of the ultrasound transducer and adjusting the output information in dependence on the acceleration signal;
   processing a sequence of ultrasound images generated by the ultrasound transducer based on different ultrasound transducer positions; and recognizing the results of the processing of the sequence of ultrasound images as a fetal body portion of the fetal body.

13. The fetal imaging method as claimed in claim 12, comprising controlling the emission power of the ultrasound transducer in dependence on a movement of the ultrasound transducer.

14. The fetal imaging method as claimed in claim 12, comprising detecting the fetal edge, and controlling the output to provide an indication of a direction to move the ultrasound transducer to move towards the fetal body or around the fetal edge.

15. The fetal imaging method as claimed in claim 12, comprising generating an output to direct the user of the method to move the ultrasound transducer to take an image of a neck region of the fetal body, and detecting a blood flow direction thereby to identify a suspected nuchal cord.

16. The fetal imaging method of claim 12, wherein at each location the ultrasound transducer passes, the method further comprises setting a maximum number of imaging pulses based on the acceleration signal.

17. A tangible, non-transitory computer readable medium that stores instructions, which when executed by a processor, cause the processor to:
   take an ultrasound image using an ultrasound transducer;
   generate an acceleration signal relating to at least one of a movement direction and a speed of the ultrasound transducer used in taking the ultrasound image;
   output information to guide a user to move the ultrasound transducer, in response to the acceleration signal, in a direction to locate a fetal edge of a fetal body;
   control an emission power of the ultrasound transducer and adjust the output information in dependence on the acceleration signal;
   process a sequence of ultrasound images generated by the ultrasound transducer based on different ultrasound transducer positions; and
   recognize results of the processed sequence of ultrasound images.

18. The tangible, non-transitory computer readable medium as claimed in claim 17 that stores further program instructions, which when executed by the processor, further cause the processor to:
   control the emission power of the ultrasound transducer in dependence on a movement of the ultrasound transducer.

19. The tangible, non-transitory computer readable medium as claimed in claim 17 that stores further program instructions, which when executed by the processor, further cause the processor to:
   detect the fetal edge, and controlling the output to provide an indication of a direction to move the ultrasound transducer to move towards a fetus or around the fetal edge of the fetus.

20. The tangible, non-transitory computer readable medium as claimed in claim 17 that stores further instructions, which when executed by the processor, further cause the processor to:
   generate an output to direct the user to move the ultrasound transducer to take an image of a neck region of a fetus, and detecting a blood flow direction thereby to identify a suspected nuchal cord.

21. The tangible, non-transitory computer readable medium as claimed in claim 17 that stores further instructions, which when executed by the processor, further cause the processor to set a maximum number of imaging pulses based on the acceleration signal.

* * * * *